(12) United States Patent
Marion, Jr.

(10) Patent No.: US 10,369,572 B2
(45) Date of Patent: *Aug. 6, 2019

(54) REAGENT DISPENSING APPARATUS

(71) Applicant: POINT OF CARE DIAGNOSTICS, LLC, Greenville, SC (US)

(72) Inventor: William Francis Marion, Jr., Greenville, SC (US)

(73) Assignee: Point of Care Diagnostics, LLC, Greenville, SC (US)

( * ) Notice: Subject to any disclaimer, the term of this patent is extended or adjusted under 35 U.S.C. 154(b) by 532 days.

This patent is subject to a terminal disclaimer.

(21) Appl. No.: 15/223,552

(22) Filed: Jul. 29, 2016

(65) Prior Publication Data

US 2017/0028401 A1 Feb. 2, 2017

Related U.S. Application Data

(60) Provisional application No. 62/199,287, filed on Jul. 31, 2015.

(51) Int. Cl.
  *B01L 3/00* (2006.01)
  *G01N 35/10* (2006.01)

(52) U.S. Cl.
  CPC .............. *B01L 3/523* (2013.01); *B01L 3/502* (2013.01); *G01N 35/1002* (2013.01); *B01L 2200/025* (2013.01); *B01L 2200/0689* (2013.01); *B01L 2200/085* (2013.01); *B01L 2200/16* (2013.01); *B01L 2300/042* (2013.01);
  (Continued)

(58) Field of Classification Search
  CPC ......... B01L 2200/16; B01L 2400/0478; B01L 2200/0689; B01L 2400/0683; B01L 3/502; B01L 3/523; G01N 35/1002
  See application file for complete search history.

(56) References Cited

U.S. PATENT DOCUMENTS 3,715,189 A  2/1973 Nighohossian et al.
4,596,556 A  6/1986 Morrow et al.
(Continued)

FOREIGN PATENT DOCUMENTS

CA  2108326     3/1997
EP  2583635 A1  4/2013
(Continued)

*Primary Examiner* — Lyle Alexander
*Assistant Examiner* — Bryan Kilpatrick
(74) *Attorney, Agent, or Firm* — Jeffrey T. Stover; Haynsworth Sinkler Boyd, P.A.

(57) ABSTRACT

A reagent dispensing apparatus includes a housing having a cavity with an opening and an aperture; and a plunger that includes a first member, that fits through the aperture, that is associated with a first seal. The plunger includes a second member associated with the first seal and a second seal that together form a first chamber, within the cavity, in which a first reagent is stored. The plunger includes a safety mechanism that controls movement of the plunger within the cavity. The apparatus includes a frangible seal that covers the opening and together with the second seal forms a second chamber, within the cavity, that stores a second reagent. When the first end is depressed and the safety mechanism is disengaged, the frangible seal is breached causing the evacuation of the first reagent or the second reagent through the opening.

22 Claims, 9 Drawing Sheets

SECTION A-A

(52) U.S. Cl.
CPC . *B01L 2300/047* (2013.01); *B01L 2300/0832* (2013.01); *B01L 2300/123* (2013.01); *B01L 2400/0478* (2013.01); *B01L 2400/0683* (2013.01)

(56) References Cited

U.S. PATENT DOCUMENTS

| | | |
|---|---|---|
| 5,257,650 A | 11/1993 | Fisk et al. |
| 5,292,307 A | 3/1994 | Dolzine et al. |
| 5,891,086 A | 4/1999 | Weston |
| 5,965,453 A | 10/1999 | Skiffington et al. |
| 6,811,341 B2 | 11/2004 | Crane |
| 8,839,982 B1 | 9/2014 | Anderson et al. |
| 8,940,539 B2 | 1/2015 | Pearcy et al. |
| 9,057,721 B1 * | 6/2015 | Marion, Jr. ........... B01L 3/5029 |
| 2005/0119589 A1 | 6/2005 | Tung et al. |
| 2005/0283132 A1 | 12/2005 | Stanus et al. |
| 2008/0099487 A1 | 5/2008 | Winn |
| 2014/0213975 A1 | 7/2014 | Clemente et al. |
| 2014/0322102 A1 | 10/2014 | Pearcy et al. |
| 2015/0080848 A1 | 3/2015 | Smith et al. |

FOREIGN PATENT DOCUMENTS

| | | |
|---|---|---|
| EP | 2703013 A1 | 3/2014 |
| WO | WO2004031048 A1 | 4/2004 |
| WO | WO2009058343 A1 | 5/2009 |
| WO | WO2012099898 A2 | 7/2012 |

* cited by examiner

Section A-A

Section A-A

SECTION A-A

SECTION A-A

SECTION A-A

Sectoin A-A

REAGENT DISPENSING APPARATUS

REFERENCE TO RELATED APPLICATIONS

This application claims priority to U.S. Provisional Patent Application No. 62/199,287, filed Jul. 31, 2015, the entire contents of the provisional application being incorporated herein by reference.

BACKGROUND

Portable, hand held, and/or disposable devices used to perform real time or near-real time medical, chemical, or biological assays may enable a user of the device, to apply one or more reagents to a sample taken from a subject (e.g., urine, saliva, feces, genitals, ear, wound, etc.). The user may perform an assay on the sample by causing the device to deliver the one or more reagents to the sample (e.g., to test for the presence of certain biological matter, chemicals, contaminants, etc.). However, a device may not properly separate reagents from one another or apply the reagents in a manner and/or order than is intended for the assay. Accordingly, the assay may be performed incorrectly, produce unreliable results, and/or waste a limited number of samples available for testing.

SUMMARY

One embodiment of the present invention is directed to a reagent dispensing apparatus for performing an assay on a sample, taken from a patient, using two or more reagents, the reagent dispensing apparatus may include a housing that includes an internal cavity having a first end with an opening and a second end that is opposite the first end. The second end may include an aperture. The reagent dispensing device may further include a plunger that includes a first member that fits through the aperture, and includes a third end and a fourth end that is opposite the third end. The third may be outside the housing, and the fourth may be located within the internal cavity and is associated with a first seal. The reagent dispensing apparatus may further include one or more safety mechanisms associated with the first member that, when engaged, prevent movement of the first member through the aperture, and, when disengaged, permit movement of the first member through the aperture. The reagent dispensing apparatus may yet further include a second member, that is within the internal cavity, having a fifth end and a sixth end that is opposite the fifth end. The fifth end may be associated with the first seal, and the sixth end may be associated with a second seal. The first seal and the second seal may form a first chamber, within a first portion of the internal cavity, that stores a first reagent. The reagent dispensing apparatus may also include a frangible seal that covers the opening of the internal cavity. The frangible seal and the second seal may form a second chamber, within a second portion of the internal cavity, that stores a second reagent. The frangible seal may be breached when the third end is depressed and the one or more safety mechanisms are disengaged to enable the plunger to move from an undepressed position to a first depressed position and causing the second reagent to exit the chamber through the opening and elute the sample. The first reagent may exit the first chamber, through the opening, to elute the sample when the one or more safety mechanisms are disengaged and the third end is further depressed to enable the plunger to move from the first depressed position to a second depressed position.

Another embodiment of the present invention is directed to a reagent dispensing apparatus that may include a housing that may include an internal cavity having a first end with an opening and a second end that is opposite the first end. The second end may include an aperture. The reagent dispensing apparatus may also include a plunger that moves through the cavity, the plunger may include a first member that includes a third end that is outside of the housing, a fourth end opposite the third end, and two or more safety mechanisms that prevent movement of the first member when the two or more safety mechanisms are engaged, the fourth end being associated with a first seal inside the internal cavity. The reagent dispensing device may also include a second member, inside the cavity, that includes a fifth end that is associated with the first seal and a sixth end, opposite the fifth end, that is associated with a second seal. The first seal and the second seal may form a first chamber, within a first portion of the internal cavity, that stores a first reagent, and the second seal may be associated with a tip. The reagent dispensing apparatus may also include a frangible seal that covers the opening of the internal cavity. The frangible seal and the second seal may form a second chamber, within a second portion of the internal cavity, that stores a second reagent. The frangible seal may be pierced when a first safety mechanism, of the two or more safety mechanisms, is disengaged and the third end is depressed to enable the plunger to move causing the tip to pierce the frangible seal and the second reagent to exit the chamber through the opening. The second seal may be broken when a second safety mechanism, of the two or more safety mechanisms, is disengaged and the third end is further depressed to enable the first reagent to exit the first chamber through the opening.

Another embodiment of the present invention is directed to a reagent dispensing apparatus that may include a housing that includes an internal cavity having a first end with an opening and second end that is opposite the first end, the second end including an aperture. The reagent dispensing apparatus may also include a plunger that is movable within the cavity. The plunger may include a first member that includes a third end, a fourth end opposite the third end, and two or more safety mechanisms. The fourth end may be associated with a first seal. The two or more safety mechanisms may include at least one of a first safety mechanism associated with a first tab that is flexible, the first safety mechanism being disengaged when the first tab is depressed, and a second safety mechanism that corresponds to a keyway associated with the aperture and second tab that is not flexible. The second safety mechanism is disengaged when the second tab is aligned with the keyway. The second member may include a fifth end that is associated with the first seal and a sixth end, opposite the fifth end, that is associated with a second seal. The first seal and the second seal may form a first chamber, within a first portion of the internal cavity, that stores a first reagent. The second seal may be associated with a tip. The reagent dispensing apparatus may also include a frangible seal that covers the opening of the internal cavity. The frangible seal and the second seal may form a second chamber, within a second portion of the internal cavity, that stores a second reagent. The frangible seal may be pierced when one of the two or more safety mechanisms is disengaged and the third end is depressed to enable the plunger to move within the cavity causing the tip to pierce the frangible seal and evacuate the second reagent from the second chamber. The second seal may be broken when a different one of the two or more safety mechanisms is disengaged and the third end is further depressed to enable the first reagent to exit the first chamber through the opening.

Another object of the present invention may include a method for administering two or more reagents to a sample in a predetermined order. The method may include providing a dispensing apparatus including a housing that includes an internal cavity having a first end with an opening and a second end that is opposite the first end. The second end may include an aperture. The method may further include providing a plunger that includes a first member that includes a third end, a fourth end opposite the third end, and one or more safety mechanisms. The third end, when depressed, may cause the first member to move through the aperture when the one or more safety mechanisms are disengaged. The fourth end may be associated with a first seal. The one or more safety mechanisms, when engaged, may prevent movement of the first member through the aperture and, when disengaged, may permit movement of the first member through the aperture. The plunger may also include a second member that includes a fifth end that is associated with the first seal and a sixth end, opposite the fifth end, that is associated with a second seal. The first seal and the second seal may form a first chamber, within a first portion of the internal cavity, that stores a first reagent. The method may also include providing a frangible seal that covers the opening of the internal cavity. The frangible seal and the second seal may form a second chamber, within a second portion of the internal cavity, that stores a second reagent. The method may also include providing a container containing a sample. The container may be capable of receiving the first reagent and the second reagent from the dispensing apparatus. The method may also include operating the dispensing apparatus to move the plunger from an undepressed position to a first depressed position to apply the second reagent to the sample. Moving the plunger from the undepressed position to the first depressed position may include ensuring the one or more safety mechanisms are disengaged, depressing the third end, breaching the frangible seal, and evacuating the second reagent from the housing through the opening to apply the second reagent to the sample. The method may also include operating the dispensing apparatus to move the plunger from the first depressed position to a second depressed position to apply the first reagent to the sample. Moving the plunger from the first depressed position to the second depressed position may include ensuring the one or more safety mechanisms are disengaged, depressing the third end, and evacuating the first reagent from the housing through the opening to apply the first reagent to the sample.

DETAILED DESCRIPTION

Figure 1:
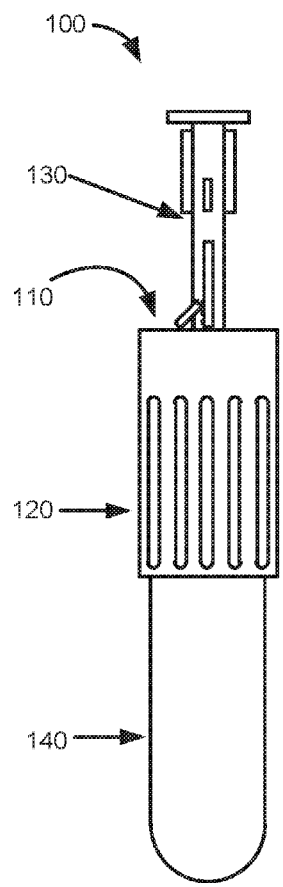
FIGS. 1 and 2 are diagrams of an example assay device having a container and a dispensing apparatus according to an implementation described herein.

FIGS. 1-9 are attached hereto and incorporated herein by this reference. The following detailed description refers to the accompanying FIGS. 1-9. The same reference numbers in different figures may identify the same or similar elements. The components illustrated in FIGS. 1-9 are provided for explanatory purposes only and the disclosure herein is not intended to be so limited. There may be additional components, fewer components, different components, or differently arranged components than illustrated in FIGS. 1-9. Also, in some implementations, one or more of the components of the dispensing apparatus may perform one or more functions described as being performed by another one or more of the components of the dispensing apparatus.

The systems, technologies, apparatus, methods and/or techniques (hereinafter, the "apparatus") may include a dispensing apparatus that may dispense one or more reagents (e.g., liquid reagents, etc.), in a predetermined order, from one or more chambers associated with the dispensing apparatus. Additionally, or alternatively, the dispensing apparatus may enable the dispense, delivery, application, saturation, etc. of one or more reagents (e.g., stored and/or contained within the apparatus, an insert, etc.) to, for example, a sample for the purpose of performing an assay operation corresponding to a medical, biological, and/or chemical analysis of the sample. The dispensing apparatus may dispense the one or more reagents in a particular order, at a particular time, and/or in a controlled manner. For example, a user may use the dispensing apparatus to dispense a first reagent to a sample by depressing a plunger of the dispensing apparatus into a housing of the dispensing apparatus until the plunger reaches a first depressed position. The user may operate the dispensing apparatus to disengage safety mechanisms (e.g. rotate the plunger and/or housing to align a tab and a key, depress tabs into an aperture in the housing, align safety mechanisms, pulling safety mechanisms, twisting safety mechanisms, etc.) associated with the plunger and/or the housing to allow a user to depress the plunger to the first depressed position. If the safety mechanisms are not disengaged, the user may not be able to depress the plunger to the first depressed position. When the user depresses the plunger to the first depressed position, the dispensing apparatus may apply the first reagent to the sample. The user may then use the dispensing apparatus to dispense a second reagent to the sample by depressing the plunger into the housing to a second depressed position. A second safety mechanism or mechanisms may need to be disengaged to permit the user to depress the plunger to the second depressed position. When the user depresses the plunger to the second depressed position, the dispensing apparatus may apply the second reagent to the sample.

The dispensing apparatus may be used in the context of human and/or non-human subjects to perform assays on a variety of sample types (e.g., urine, feces, genitals, ear, wound, etc.). For example, the sample to be tested may be obtained from a human, non-human animal, or inanimate objects (e.g., a surface, soil, plant, etc.). Additionally, or alternatively, the dispensing apparatus may be made in various sizes and/or shapes to accommodate or house different quantities and/or different types of reagents. The dispensing apparatus may also, or alternatively, operate in a range of environment and/or climates, and/or preserve the sterility the reagents, components that contact such reagents and/or a sample.

Figure 2:
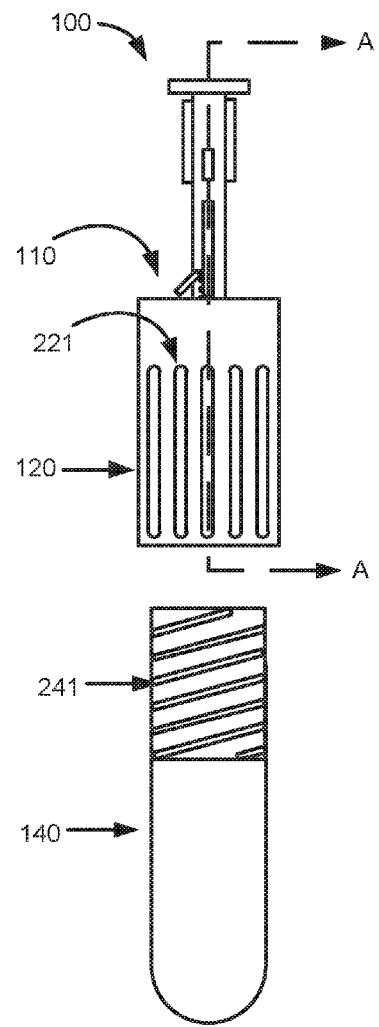

FIGS. 1 and 2 are diagrams of an example assay device having a container and a dispensing apparatus according to an implementation described herein. As shown in FIG. 1, the assay device 100 may include a group of components, such as a dispensing apparatus 110 and a container 140. The number of components, illustrated in FIG. 1, is provided for explanatory purposes only. In practice, there may be additional components, fewer components, different components, or differently arranged components than illustrated in FIGS. 1 and 2. For example, while container 140 is depicted in FIGS. 1 and 2 as being a connectable to dispensing apparatus, additionally, or alternatively, container may not connect to, attach to or make contact with dispensing apparatus 110. Also, in some implementations, one or more of the components of assay device 100 may perform one or more functions described as being performed by another one or more of the components of assay device 100.

Dispensing apparatus 110 may include a housing 120 and a plunger 130. The housing 120 may store and/or contain one or more reagents in one or more chambers, as further described herein. Plunger 130 may be temporarily or permanently attached to and/or inserted into the housing 120, may separate two or more reagents stored within and/or partially within the housing 120 and/or may enable the release of one or more reagents from one or more chambers associated with the housing, as further described herein. Container 140 may be connectable to the housing 120 (and/or other component of the dispensing apparatus 110), such as by using one or more attachment mechanisms, such as, for example, threaded connection, mechanical fastener, clip, magnet, adhesive, buttons, male-female connections, any combination thereof, or any other mechanism that may enable secure attachment. Additionally, or alternatively, container 140 may not make connect to, or make contact with, dispensing apparatus 100. In the non-limiting example depicted in FIG. 2, container 140 may include threads 241 that may be used to connect container 140 to a gap in the housing 120 as later described herein. Housing 120 may include one or more ridges 221 which may provide a bearing surface and/or increase the grip of a user to assist the user when attaching housing 120 to container 140 or removing housing 120 from container 140.

Housing 120 may be formed by a material or materials of sufficient rigidity and strength to support the weight of the plunger 130, other components, to store reagents and/or any static and/or dynamic loads (e.g., forces, torques, tensions, compressions, etc.) imparted on the housing 120 during packaging, shipment, and/or while using the dispensing apparatus 110, such as when a plunger 130 is depressed, causing reagent to evacuate dispensing apparatus 110 (as further described herein). Housing 120 may, for example, be made of polymer, metal, composite, glass, wood, or some combination thereof. Housing 120 may also, or alternatively, include transparent or translucent material, for example to enable the presence, type, quantity, quality, etc. of a reagent to be observed by a user. The strength and/or rigidity of the material may enable the housing 120 to maintain a basic shape when being used and/or to enable various components to be attached to the housing 120 and to be used. The housing 120 may assume any shape or volume such as, for example, a cylinder, cube, orthotope, rectangular cuboid, rectangular parallelepiped, three dimension polygon, etc. Additionally, or alternatively, the contours of the housing 120 may be straight and/or curved in a concave and/or convex manner.

Plunger 130 may be formed by a material or materials of sufficient rigidity and strength to support the weight of the housing 120, other components, to enable reagents to be stored, and/or any static and/or dynamic loads (e.g., forces, torques, tensions, compressions, etc.) imparted on the plunger 130 while using the dispensing apparatus 110, such as a depression force. Plunger 130 may, for example, be made of polymer, metal, composite, wood, or some combination thereof. Plunger 130 may also, or alternatively, include transparent or translucent material, for example to enable the presence, type, quantity, quality, etc. of a reagent to be observed by a user. The strength and/or rigidity of the material may enable plunger 130 to maintain a basic shape when being used and/or to enable various components to be attached to plunger 130 and to be used. Plunger 130 may assume any shape or volume. Additionally, or alternatively, the contours of the plunger 130 may be straight and/or curved in a concave and/or convex manner.

Container 140 may be formed by a material of sufficient rigidity and strength to support the weight of the housing 120, other components, to withstand connecting the container 140 to dispensing apparatus 110, to enable samples and reagents to be stored, and/or any static and/or dynamic loads (e.g., forces, torques, tensions, compressions, etc.) imparted on the container while using the dispensing apparatus 110, such as a depression force. Container 140 may, for example, be made of polymer, metal, composite, wood, or some combination thereof. Container 140 may also, or alternatively, include transparent or translucent material, for example to enable the presence, type, quantity, quality, etc. of a reagent to be observed by a user or to permit a measuring device (a luminometer, etc.) to analyze the contents of the container. The strength and/or rigidity of the material may enable container 140 to maintain a basic shape when being used and/or to enable various components to be attached to container 140 and to be used. Container 140 may assume any shape or volume. Additionally, or alternatively, the contours of the container 140 may be straight and/or curved in a concave and/or convex manner.

Figures 3A, 3B:
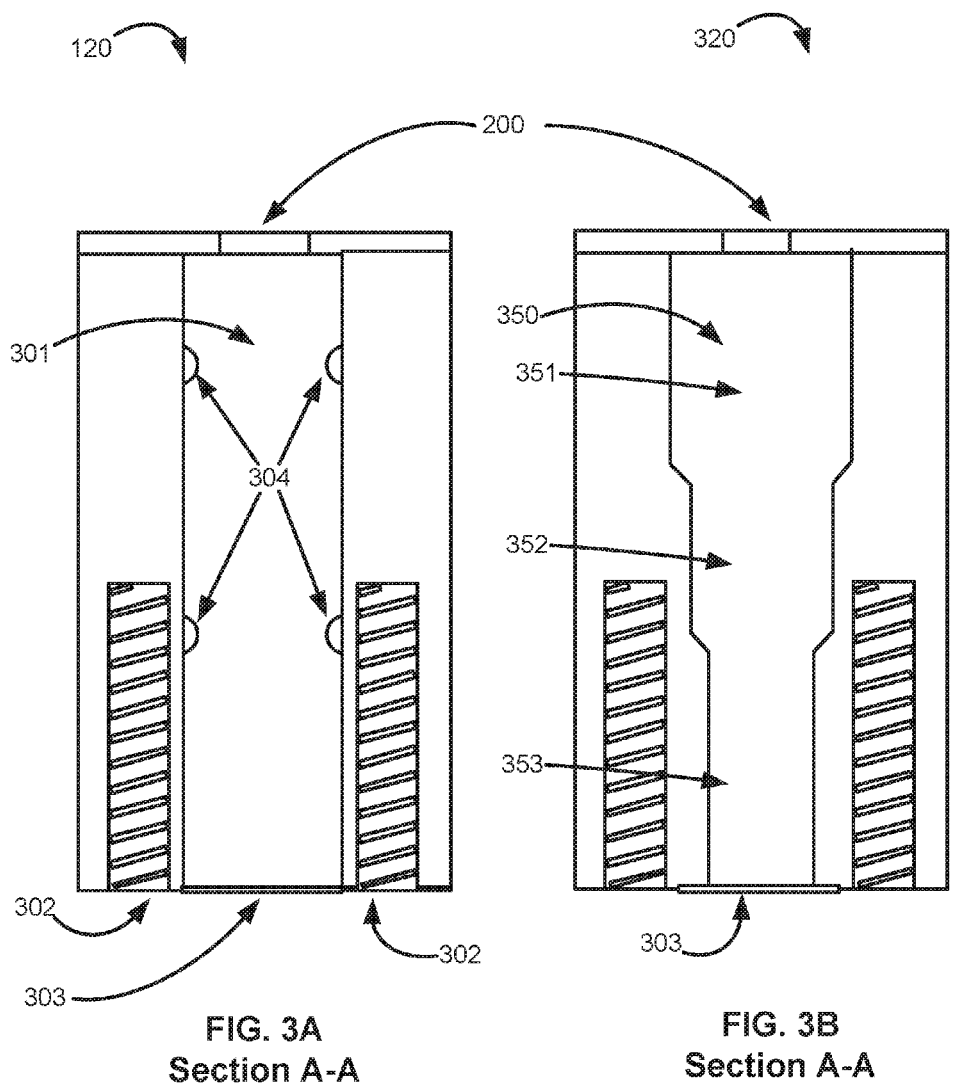
FIGS. 3A and 3B are diagrams of example housings of dispensing apparatuses according to an implementation described herein.

FIGS. 3A and 3B are diagrams of example housings of dispensing apparatuses according to an implementation described herein. As shown in FIG. 3A, housing 120 may include a cavity 301, a gap 302, a frangible seal 303 and one or more protrusions 304. The number of components, illustrated in FIG. 3A, is provided for explanatory purposes only. In practice, there may be additional components, fewer components, different components, or differently arranged components than illustrated in FIG. 3A. Also, in some implementations, one or more of the components of housing 120 may perform one or more functions described as being performed by another one or more of the components of housing 120.

Cavity 301 may include an interior cavity with a first end, and a second end that is opposite the first end. The first end may be covered with a seal, such as frangible seal 303 (e.g., such as aluminum foil, mylar, polymer film, or some other material that can form a sterile, an airtight, and/or liquid tight seal) (hereinafter, a "first seal") that does not react with a reagent. The second end may be open to allow a plunger 130 to be inserted through the aperture 200 (e.g., during manufacture, assembly, use, thereafter, etc.).

In one embodiment, the housing 120 may be a cylindrical shape, and the cavity 301 may also be a cylindrical shape and may be formed inside housing 120. Additionally, or alternatively, housing 120 may assume any shape or volume such as, for example, a cylinder, cube, sphere, orthotope, rectangular cuboid, rectangular parallelepiped, three dimension polygon, etc. Additionally, or alternatively, the contours of the housing 120 may be straight and/or curved in a concave and/or convex manner. Similarly, cavity 301 may assume any shape or volume such as, for example, a cylinder, cube, orthotope, rectangular cuboid, rectangular parallelepiped, three dimension polygon, etc. Additionally, or alternatively, the contours of the cavity 301 may be straight and/or curved in a concave and/or convex manner. Additionally, or alternatively, cavity 301 may be formed in a truncated conical shape in which the cross-sectional area of the cavity 301 increases from one end of the cavity proximate the frangible to an opposite end of the cavity.

Gap 302 may receive a container, such as container 140, and/or connect the container to the dispensing device 110 (e.g. threaded attachment, compression fit, adhesives, etc.). Container may surround all or a portion of cavity 301. Additionally, or alternatively, gap 302 may include one or more protrusions through which a fastener (e.g. screw, rivet, nail, etc.) may be placed to connect a container to housing 120. Gap 302 may include a first end and a second end opposite the first end. The first end may be open to allow a container to be inserted into housing 120. The container, such as container 140 of FIGS. 1A and 1B, may, for example, contain a sample and/or allow insert of a sample into the container 140 such that a reagent may be released from dispensing apparatus 110 into the container 140 and/or applied to the sample.

Housing 120 may include one or more protrusions 304 which may decrease the diameter of the cavity 301. Protrusions 304 may be any size or shape (etc. circular, triangular, square, dimples, etc.) and may depend from the cavity 301. Protrusions 304 may encircle the inner surface of cavity 301. Additionally, or alternatively, protrusions 304 may take the form of one or more separated indentations within the cavity 301, which reduce the width of the cavity 301. Because protrusions 304 decrease the width of the cavity 301, protrusions 304 increase the force required for a user to operate plunger 130 of a dispensing apparatus 110 from an undepressed position to a first depressed position and/or from a first depressed position to a second depressed position, etc. by increasing the amount of force required to depress the plunger 130. This increase in force may alert a user that the dispensing apparatus 110 is dispensing and/or will soon dispense a reagent as described herein. Protrusions 304 may be formed as part of housing 120. Additionally, or alternatively, protrusions 304 may be connected (e.g. by fastening, welding, adhesives, mechanical fasteners, etc.) to housing 120.

In an alternative arrangement shown in FIG. 3B, housing 320 may include a cavity 350 that may include a non-uniform cross section including a first section 351, a second section 352 and a third section 353. The number of components, illustrated in FIG. 3B, is provided for explanatory purposes only. In practice, there may be additional components, fewer components, different components, or differently arranged components than illustrated in FIG. 3B. Also, in some implementations, one or more of the components of housing 320 may perform one or more functions described as being performed by another one or more of the components of housing 320.

A reagent may reside in the first cavity 351, second cavity 352 and/or the third cavity 353. The second section 352 may be narrower than the first section 351. The third section 353 may be narrower than the section 352. The force required for a user to operate plunger 130 of a dispensing apparatus 110 from an undepressed position to a first depressed position and/or from a first depressed position to a second depressed position may increase as a seal and/or sealing surface, as later described herein, passes from the first section 351 to the second section 352 and/or from the second section 352 to the third section 353. This increase in force may alert a user that the dispensing apparatus 110 is dispensing and/or will soon dispense a reagent as described herein.

Additionally, or alternatively, other implementations need not be so limited. For example, in other implementations the housing need not include protrusions and/or may include a one or more sections of consistent and/or inconsistent cavity diameters.

Figure 4A:
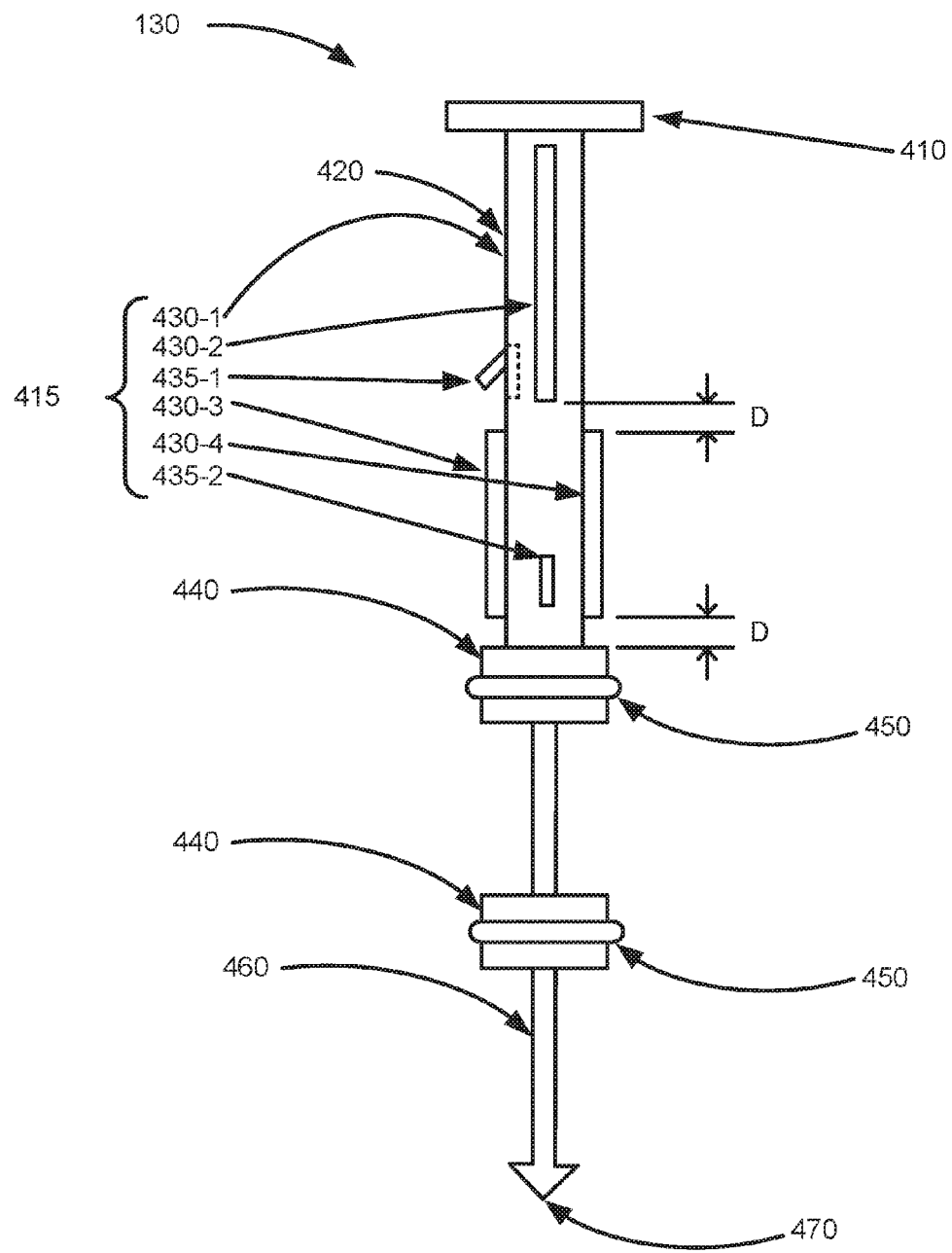
FIG. 4A is a diagram of an example plunger apparatus according to an implementation described herein.

FIG. 4A is a diagram of an example plunger 130. As depicted in FIG. 1, plunger 130 may include a cap 410, a first member 420, one or more safety mechanisms 415, one or more flanges 440 (referred to individually as "flange 440" or collectively as "flanges 440"), one or more seals 450 (referred to individually as "seal 450" or collectively as "seals 450"), a second member 460 and a tip 470. The number of components, illustrated in FIG. 4A, is provided for explanatory purposes only. In practice, there may be additional components, fewer components, different components, or differently arranged components than illustrated in FIG. 4A. Also, in some implementations, one or more of the components of plunger 130 may perform one or more functions described as being performed by another one or more of the components of plunger 130.

Cap 410 may provide a bearing surface to a user when the plunger 430 is depressed into a housing 120 and/or retracted from a housing 120. For example, a user may depress the plunger 130 into housing 120 by placing a finger and/or thumb on the cap and applying a force on an upper surface of the cap, which upper surface resides opposite the first member 420.

Cap 410 may be formed by a material or materials of sufficient rigidity and strength to support a user depressing cap 410, to withstand the depression force created by a user when the safety mechanisms are not disengaged, as described later herein, to support the weight of the dispensing apparatus 110 and container 140, and/or any static and/or dynamic loads (e.g., forces, torques, tensions, compressions, etc.) imparted on the cap 410 while using the dispensing apparatus 110. Cap 410 may, for example, be made of polymer, metal, composite, wood, or some combination thereof. The strength and/or rigidity of the material may enable cap 410 to maintain a basic shape when being used and/or to enable various components to be attached to cap 410 and to be used. Cap 410 may assume any shape or volume. Additionally, or alternatively, the contours of the cap 410 may be straight and/or curved in a concave and/or convex manner. Cap 410 may be connected (e.g. welded, formed as a part of, adhesives, mechanical fasteners, etc.) to first member 420. Cap 410 may be connected to first member before or after plunger 130 and housing 120 are assembled.

First member 420 may be formed by a material or materials of sufficient rigidity and strength to support the weight of the dispensing apparatus 110 and container 140 as well as other components, to withstand connecting the container 140 to dispensing apparatus 110, to enable samples and reagents to be stored, to withstand the forces associated with engaging and disengaging safety mechanisms 415, and/or any static and/or dynamic loads (e.g., forces, torques, tensions, compressions, etc.) imparted on first member 420 while using the dispensing apparatus 110, such as a depression force. First member 420 may, for example, be made of polymer, metal, composite, wood, or some combination thereof. The strength and/or rigidity of the material may enable first member 420 to maintain a basic shape when being used and/or to enable various components, such as safety mechanisms 415, to be attached to first member 420 and to be used. First member 420 may assume any shape or volume. First member 420 may be shaped to permit first member 420 to move through an aperture located on housing 120. The contours of first member 420 may be straight and/or curved in a concave and/or convex manner.

First member 420 may have a first end connected to cap 410 and a second end connected to flange 440. First member may include one or more safety mechanisms 415. First member 420 may pass through an opening in housing 120, such as aperture 400, when a user operates dispensing apparatus 110 from an undepressed position to a first depressed position and/or from a first depressed position to a second depressed position, etc.

Safety mechanisms 415 may include one or more safety tabs 430 (hereinafter referred to collectively as "tabs 430", individually as "tab 430", or specifically as tab 430-1, 430-2, ... 430-N, etc.), one or more safety flexible tabs 435 (hereinafter referred to collectively as "flexible tabs 435", individually as "flexible tab 435", or specifically as flexible tab 435-1, 435-2, ... 435-N, etc.), and/or any other mechanism or device that may reside on plunger 130 and/or housing 120 and may prevent dispensing apparatus 110 from being depressed and/or retracted unless safety mechanism is disengaged, as described herein. For example, and not as a limitation, safety mechanisms 415 may include removable pins, flexible tabs, breakable mechanisms, removable rings, etc. Safety mechanisms 415 may control movement of the plunger within the housing, which control may be accomplished through engaging and/or disengaging the safety mechanisms as described herein. Safety mechanisms 415 may prevent a reagent from being evacuated prematurely and/or unintentionally, such as during shipping, handling, etc. (e.g., by preventing the tip 470 from penetrating the frangible seal as later described) by preventing first member 420 from moving through an opening in housing 120, such as aperture 400, unless tabs are depressed, properly aligned, and/or otherwise operated to permit first member 420 to pass through an opening in housing 120, such as keyway 202 of aperture 200.

Safety mechanisms 415 may be formed by a material or materials of sufficient rigidity and strength to support the forces associated with operating (e.g. depressing, aligning, rotating, etc.) safety mechanisms 415, depressing plunger 130 with and without disengaging safety mechanisms 415, to withstand connecting container 140 to dispensing apparatus 110 and/or any static and/or dynamic loads (e.g., forces, torques, tensions, compressions, etc.) imparted on safety mechanisms 415 while using the dispensing apparatus 110. Safety mechanisms 415 may, for example, be made of polymer, metal, composite, wood, or some combination thereof. The strength and/or rigidity of the material may enable safety mechanisms 415 to maintain a basic shape when being used. The plasticity of the material may enable safety mechanisms 415 to be temporarily deformed during use but to return to an original size and shape after use. Safety mechanisms 415 may assume any shape or volume. Safety mechanisms 415 may be shaped to move through an aperture and/or keyway located on housing 120. Safety mechanisms may be connected to (e.g. weldments, adhesives, mechanical fasteners, press fit, etc.) or formed as part of plunger 130 and/or housing 120.

Tabs 430 may be connected to first member 420 and may protrude from a surface of first member 420. As depicted in FIG. 4A, a set of tabs may be comprised of one tab, tab 430-3, which resides directly across from another tab, such as 430-4, on opposite sides of first member 420. Additionally, or alternatively, a set of tabs 430 may be two or more tabs configured to move through a keyway located on housing 120. Additionally, or alternatively, a set of tabs, such as tab 430-1 and tab 430-2, may reside 90 degrees from another set of tabs, tab 430-3 and tab 430-4, located on first member 420. When tabs 430 are located 90 degrees from other tabs on first member 420, tabs may reside a longitudinal distance D along first member 420 from other tabs 430 on first member 420. Longitudinal distance D may be greater than or equal to the thickness of an upper surface of housing 120, such as surface 403 described in FIG. 4B. Additionally, or alternatively, tabs 430 may be located longitudinal distance D along first member 420 from flange 440.

A user may depress, shift or apply force to the tab 430, housing 120, container 140 and/or plunger 130 in a manner that causes tabs 430 to align with and/or enter aperture or keyway within housing 120. When tab 430 is in this position, tabs may be disengaged to enable plunger 130 to further move into and/or enter the cavity, such as cavity 301, of housing 120. Thus, tab 430 may prevent tip 470 from inadvertently contacting and/or penetrating frangible seal, may prevent dispensing apparatus 110 from moving from an undepressed position to a first depressed position, may prevent dispensing apparatus 110 from moving from a first depressed position to a second depressed position, etc. Additionally, or alternatively, tabs 430 may prevent the retraction of plunger 130 from housing 120.

Flexible tabs 435 may be connected (e.g. pinned, welded, formed as a part of, fastened, etc.) to first member 420 and may protrude from a surface of first member 420. A user may depress, shift or apply force to flexible tabs 435, housing 120, container 140 and/or plunger 130 in a manner that causes flexible tabs 435 to align with and/or enter aperture or keyway within housing 120 to disengage flexible tabs 435. Additionally, or alternatively, flexible tabs 435 may include a void within first member 420 into which void flexible tabs 435 may be depressed to disengage flexible tabs. When flexible tabs 435 are disengaged, plunger 130 may be enables to further move into and/or enter the cavity, such as cavity 301, of housing 120. Thus, flexible tabs 435 may prevent tip 470 from inadvertently contacting and/or penetrating frangible seal, may prevent dispensing apparatus 110 from moving from an undepressed position to a first depressed position, may prevent dispensing apparatus 110 from moving from a first depressed position to a second depressed position, etc. Additionally, or alternatively, flexible tabs 435 may prevent the retraction of plunger 130 from housing 120.

Flanges 440 may be formed by a material or materials of sufficient rigidity and strength to support the forces associated with operating (e.g. depressing, aligning, rotating, etc.) safety mechanisms 415, depressing plunger 130 with and without disengaging safety mechanisms 415, forces associated with maintaining a barrier between chambers, and any other static and/or dynamic loads (e.g., forces, torques, tensions, compressions, etc.) imparted on flanges 440 while using the dispensing apparatus 110. Flanges 440 may, for example, be made of polymer, metal, composite, wood, or some combination thereof. The strength and/or rigidity of the material may enable flanges 440 to maintain a basic shape when being used. The plasticity of flanges 440 may enable flanges 440 to be temporarily deformed during use, such as when moving past protrusions as will be later described, but to return to an original size and shape after use. Flanges 440 may assume any shape or volume. Flanges 440 may expand or contract to conform to a volume within which flanges 440 reside, such as cavity 301, which may flanges 440 to form a sterile, airtight and/or liquid-tight seal within a cavity of housing 120. Flanges 440 may be connected to (e.g. weldments, adhesives, mechanical fasteners, press fit, etc.) or formed as part of plunger 130 and/or any component of plunger 130 described herein.

Flanges 440 may be connected to first member 420 and/or second member 460 and may provide the surface on which seal 450 resides. Additionally, or alternatively, seals 450 may be formed as part of flanges 440. Additionally, or alternatively, flanges 440 may make contact with an interior surface of a cavity of a housing 120 to form a sterile, an airtight, and/or liquid tight seal, within a cavity, such as cavity 301, of a housing 120 as described herein when plunger 130 is placed within housing 120, which eliminates the need for seal 450. Flange 440 may be designed to fit within a cavity, such as cavity 301 and/or cavity 350 of FIG. 3. Flange 440 may be formed (e.g. have a groove, a notch, etc.) to secure a seal 450.

Seal 450 may include various types of sealing mechanisms. Seal 450 may make contact with an interior surface of a cavity of a housing 120 to form a sterile, an airtight, and/or liquid tight seal, within a cavity, such as cavity 301, of a housing 120 as described herein when plunger 130 is placed within housing 120. Seals 450 may be connected to first member 420, second member 460 and/or flanges 440 and may be located around the perimeter of flanges 440. Seals 450 may allow a cavity within a housing 120 to store and/or contain one or more reagents, may prevent the reagents from leaking out of or prematurely exiting the cavity, and/or may separate the cavity 301 into two or more chambers. Seal 450 may be temporarily and/or permanently attached to flange 440. Seal 450 may be any form or material (e.g., rubber seals, extrusions, lathe-cuts, gaskets, O-rings, packing, Teflon® seals, mechanical seals, graphite, cloth, metal seals, metal rings, oil seals, elastomer seals, piston seals, quad rings, etc.) that may form a seal within a cavity. The configuration and type of seal shown in FIG. 4A is not intended to be exhaustive or to limit the implementations to the precise form disclosed.

In one non-limiting implementation, when the plunger 130 is depressed into the cavity 301 (e.g., when a user depresses the cap 410 with his or her thumb, forefinger, etc.), by a particular distance, seal 450 may move further through the cavity (of the housing), which may enable the reagent stored within a chamber formed by seals 450 and/or the cavity 301 to move through the cavity. As plunger 130 continues to be depressed into the cavity, tip 470 may pierce through and/or break open the frangible seal, as described later herein. Seals 450 may force a reagent to be evacuated from the dispensing apparatus 110 through the pierced frangible seal (e.g., in a manner similar to how a syringe operates) and/or may enable a second reagent to move from an undepressed position to a depressed position, from a first depressed position to a second depressed position, etc.

Second member 460 may be formed by a material or materials of sufficient rigidity and strength to support the forces associated with operating (e.g. depressing, aligning, rotating, etc.) the dispensing apparatus 110, depressing plunger 130 with and without disengaging safety mechanisms 415, to withstand breaking a frangible seal, and/or any static and/or dynamic loads (e.g., forces, torques, tensions, compressions, etc.) imparted on second member 460 while using the dispensing apparatus 110. Second member 460 may, for example, be made of polymer, metal, composite, wood, or some combination thereof. The strength and/or rigidity of the material may enable second member 460 to maintain a basic shape when being used. Second member 460 may assume any shape or volume. Second member 460 may be shaped to fit within a cavity and sized to permit a volume of reagent to be stored within a chamber. Second member 460 may be connected to (e.g. weldments, adhesives, mechanical fasteners, press fit, etc.) plunger or formed as part of plunger 130 and/or any of its components described herein.

Second member 460 may be connected to one or more flanges 440 and tip 470, and may be longitudinally aligned with first member 420. When the dispensing device 110 is undepressed, as described herein, second member may reside within cavity 301 of housing 120. Tip 470 may include and/or form a mechanism that that is sufficiently sharp to easily penetrate and/or break a seal (e.g., frangible seal of FIG. 3A). For example, tip 470 may include a point, conical shape, knife, etc.

Figure 4B:
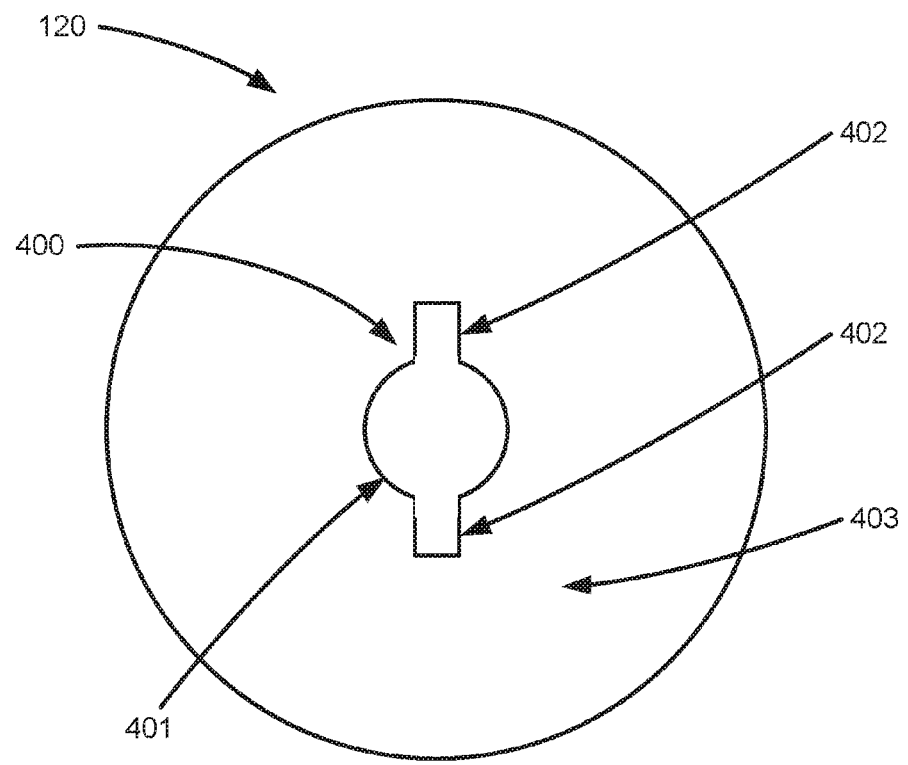
FIG. 4B is a diagram of an example housing of the dispensing apparatus of FIGS. 1A and 1B according to an implementation described herein.

FIG. 4B is a diagram of housing 120 of the dispensing apparatus of FIGS. 1 and 2. Housing 120 may include an aperture 400 formed on an upper surface 403 of the housing 120 through with upper surface 403 a plunger may move. Aperture 200 may be any size and/or shape (e.g. circular, rectangular, pentagon, etc.). Upper surface 403 may define a thickness that is less than or equal to a distance, such as distance D, between sets of safety tabs located on the plunger, as later described. Aperture 200 may include a center 201 and a keyway 202. Plunger 130 may pass through aperture 200 to move from an undepressed position to one or more depressed position as described herein. Safety mechanisms 415 may be aligned, depressed or otherwise operated to pass through keyway 202 and/or center 201 to move dispensing apparatus 110 from an undepressed position to a first depressed position, from a first depressed position to a second depressed position, etc.

Figure 5:
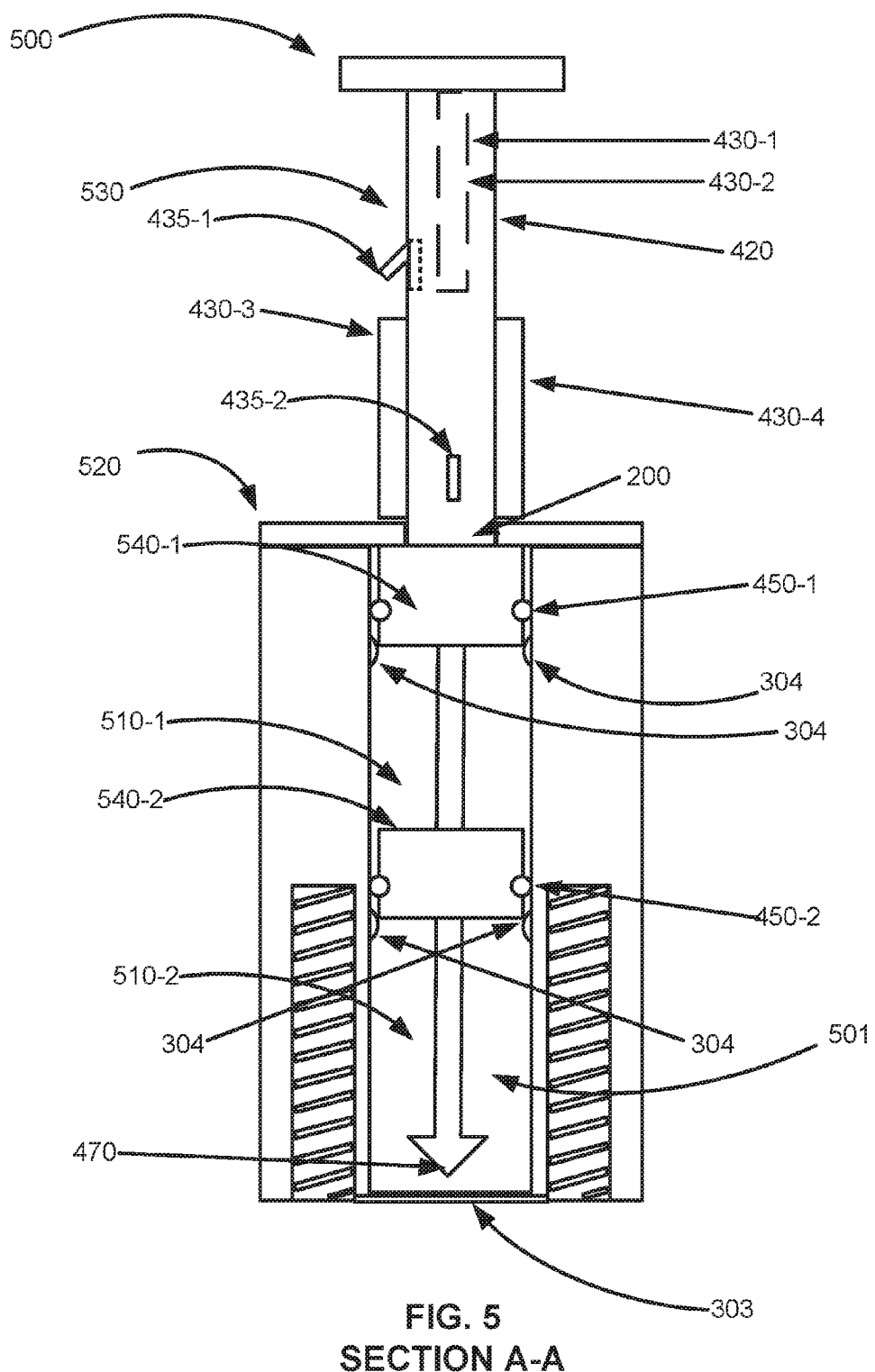
FIG. 5 is a diagram of an example dispensing apparatus in an undepressed position according to an implementation described herein.

FIG. 5 is a diagram of an example dispensing apparatus 500 that may include two chambers 510 and may be positioned in an undepressed position. As depicted in FIG. 5, dispensing apparatus 500 may include a plunger 530 and a housing 520. The number of components, illustrated in FIG. 5, is provided for explanatory purposes only. In practice, there may be additional components, fewer components, different components, or differently arranged components than illustrated in FIG. 5. Also, in some implementations, one or more of the components of dispensing apparatus 500 may perform one or more functions described as being performed by another one or more of the components of dispensing apparatus 500.

Figure 8:
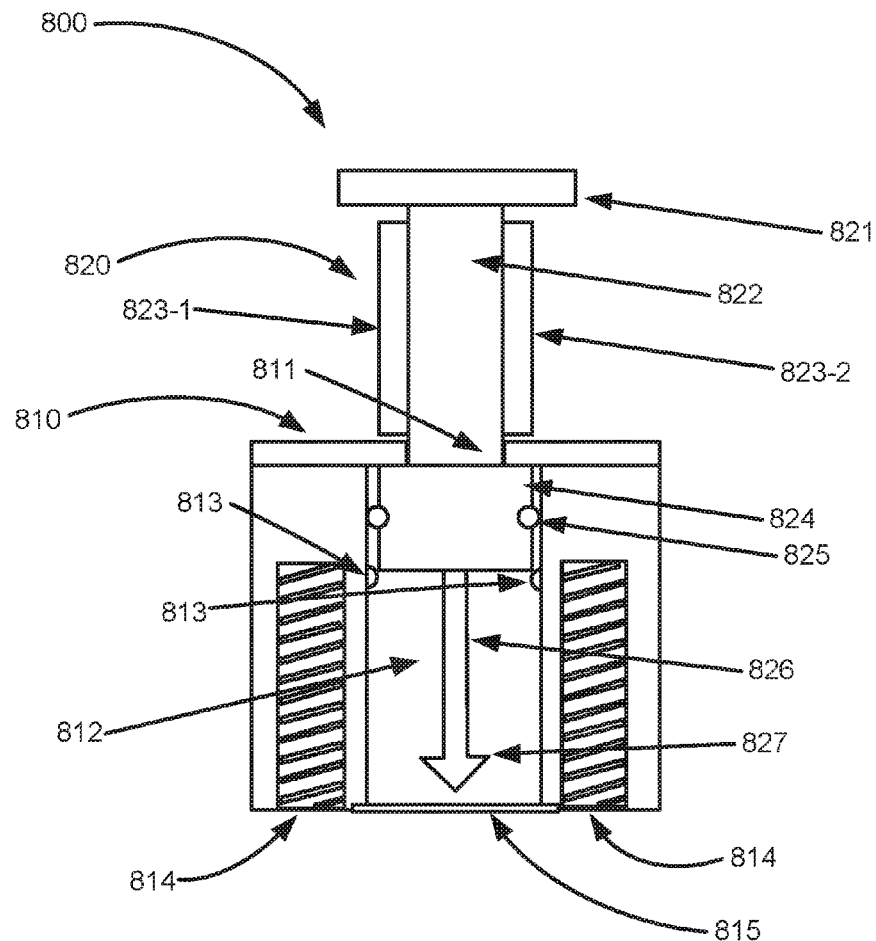
FIG. 8 is a diagram of an example dispensing apparatus with one chamber according to an implementation described herein.

FIG. 5 depicts dispensing apparatus 500 with plunger 130 in an undepressed position, where tip 470 is located inside cavity 501. In this position, housing 520 in cooperation with plunger 530 form the chambers 510 within which reagents may be stored. A first chamber 510-1 may be formed within a portion of cavity 501 between first flange 540-1 and second flange 540-2, and a second chamber 510-2 may be formed within a portion of cavity 501 between second flange 540-2 and frangible seal 303. The number of chambers formed within a cavity vary depending upon the number of seals 450 and/or flanges 540. The number of chambers may be equivalent to the number of flanges of a plunger. Alternatively, the number of chambers may be greater than or less than the number of flanges of a plunger. For example, if second flange 542 is removed, then dispensing apparatus would have only one chamber, as depicted in FIG. 8. Additionally, or alternatively, if an additional flange is added to the second member between first flange 540-1 and second flange 540-2, then dispensing apparatus may have three chambers.

A first reagent may be stored within in first chamber 510-1, and a second reagent may be stored within second chamber 510-2. First seal 450-1 of first flange 540-1 may form a barrier between first chamber 510-1 and the portion of cavity 501 located opposite first seal 450-1 to preclude the first reagent from flowing from the first chamber 510-1 to the other side of first seal 450-1 and out of aperture 200. Additionally, or alternatively, an additional frangible seal may be located proximate first seal 450-1 to prevent first reagent from flowing from first chamber 510-1. Second seal 450-2 may preclude the second reagent from flowing from the second chamber 510-2 to first chamber 510-1 and/or may preclude the first reagent from flowing from the first chamber 510-1 to the second chamber 510-2. Additionally, or alternatively, an additional frangible seal (not shown) may be located proximate second seal 450-2 to form a barrier between first chamber 510-1 and second chamber 510-2.

As depicted in FIG. 5, the first chamber 510-1 and the second chamber 510-2 may be longitudinally aligned along plunger 530. This longitudinal alignment may enable the reagents to be evacuated from the dispensing device 500 in a predetermined order by requiring the reagent in the second chamber 510-2 to be evacuated from the dispensing device 500 before the reagent in the first chamber 510-1.

Protrusion 304 may contact first flange 540-1, second flange 540-2 and/or seals 450 and may reduce the width of the cavity 501 which may increase the resistance to depressing plunger 530 from a depressed position to a first undepressed position and/or from a first depressed position to a second undepressed position, as later described herein. A user may be required to apply a force to the plunger to enable the flanges 540 and/or seals 450 to move past the protrusions 304. In this way, protrusions 304 may prevent the plunger 530 of the dispensing apparatus 500 from accidentally and/or inadvertently moving from the undepressed position to a first depressed position, from a first depressed position to a second depressed position, etc. Additionally, or alternatively, the increased force required for a user to operate the dispensing apparatus 500 due to protrusions 304 may alert the user that dispensing apparatus 500 is moving from the undepressed position to a first depressed position, from a first depressed position to a second depressed position, etc.

Tabs 430 may preclude plunger 530 from moving through aperture 200 unless tabs 430 are depressed, properly aligned, and/or otherwise operated to allow tabs 430 to pass through aperture 200. In one embodiment, tabs 430 may be aligned with aperture 200 by rotating plunger 530 and/or housing 520 and/or a container.

Flexible tabs 435 may preclude plunger 530 from moving through aperture 200 unless flexible tabs 435 are depressed, properly aligned and/or otherwise operated to allow flexible tabs 435 to pass through aperture 200. By restricting the plunger 130 from being depressed, tabs 430 and flexible tabs 435 may prevent the dispensing apparatus 500 from accidentally and/or inadvertently moving from the undepressed position to a first depressed position, from a first depressed position to a second depressed position, from a second depressed position to a third depressed position (not shown), etc.

Figure 6:
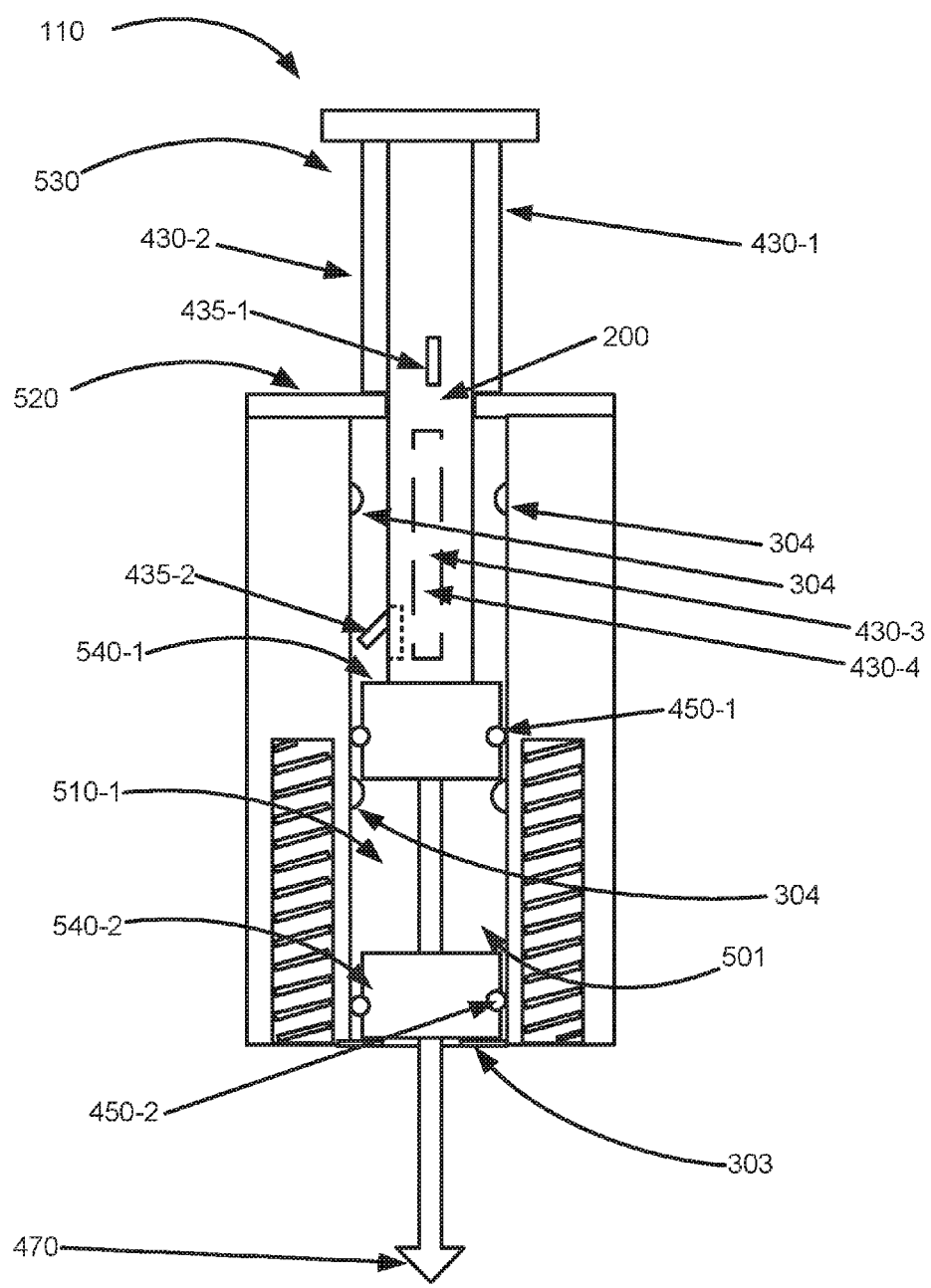
FIG. 6 is a diagram of the example dispensing apparatus of FIG. 5 in a first depressed position.

FIG. 6 is a diagram of the example dispensing apparatus 500 of FIG. 5 in a first depressed position. As depicted in FIG. 6, depressing the plunger 530 to a first depressed position may enable the tip 470 to pierce, break, displace, etc. the frangible seal 303, causing the second reagent in second chamber 510-2 to evacuate the second chamber 520 as the second chamber 510-2 exits the dispensing apparatus 500 and/or to elute (e.g. applied to, mix with, etc.) a sample. Alternatively, depressing the plunger 530 to a first depressed position may breach (e.g. rupture, disconnect, unseal, burst, pierce with tip 470, etc.) the frangible seal 303, even in absence of tip 470, by compressing the volume of second chamber 510-2, which increases the pressure seen by the frangible seal. Additionally, in the first depressed position, the first reagent in first chamber 510-1 is moved along cavity 501 to or near the position occupied by first chamber 510-1 when plunger 530 is in the undepressed position. Depressing the plunger 530 from the undepressed position to the first depressed position may require a user to disengage safety mechanisms and/or ensure safety mechanisms are in a disengaged position, which may require a user to operate the plunger 530 to permit tab 430-3 and tab 430-4 to pass through aperture 200, which may include a keyway (not shown), and/or may require a user to depress flexible tab 435-2 to permit flexible tab 435-2 to pass through aperture. Depressing the plunger 530 from the undepressed position to the first depressed position may also require the user to apply sufficient force to plunger 530 to enable first flange 541, second flange 542 and seals 450 to move past protrusions 304. The user may determine that the dispensing apparatus 110 is in the first depressed position when the first flange 541 and/or the seal 450-1 associated with first flange contacts protrusions 304 and/or when tab 430-1, tab 430-2 and/or flexible tab 435-1 contacts an upper surface of housing 520.

Figure 7:
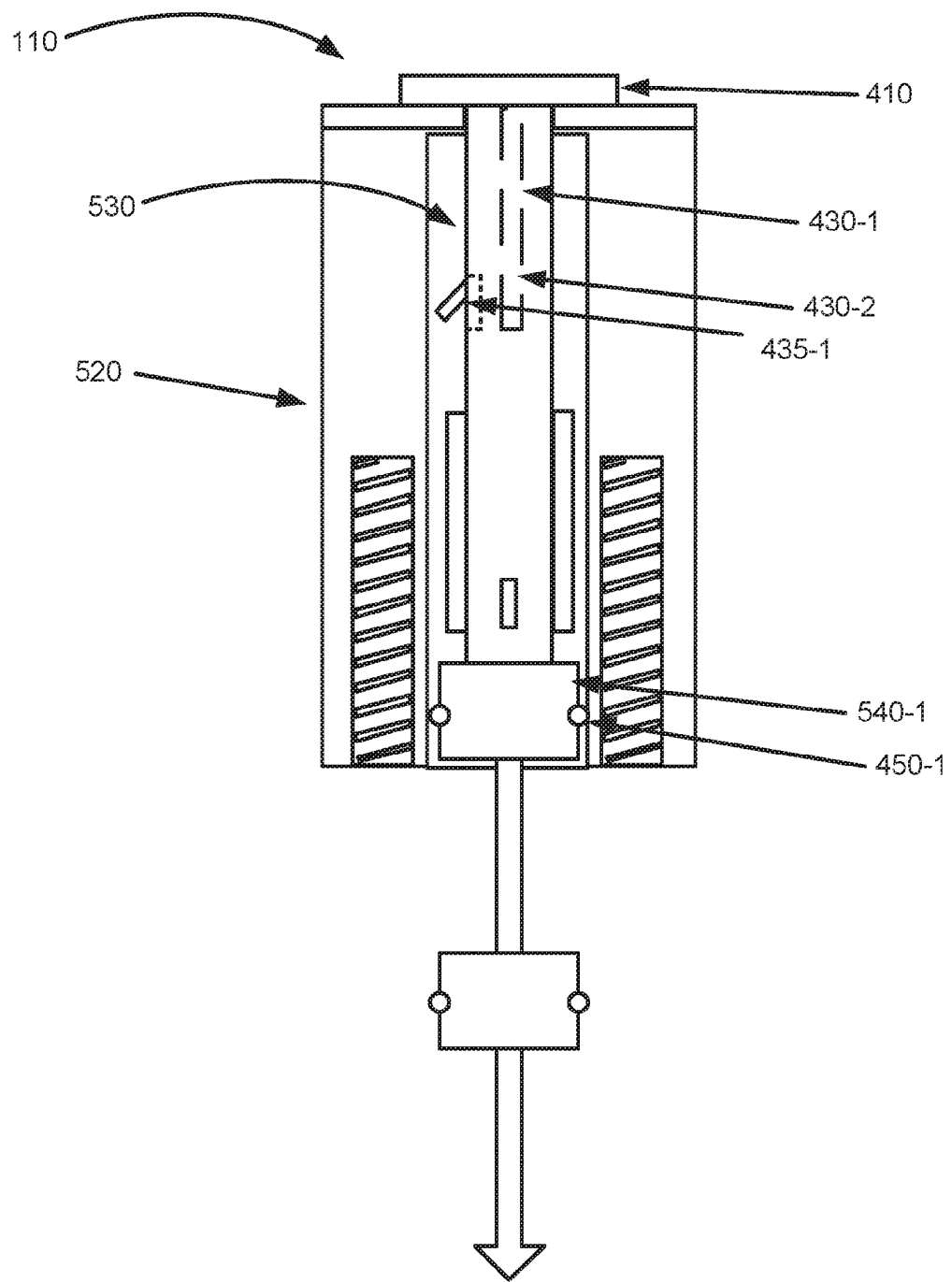
FIG. 7 is a diagram of the example dispensing apparatus of FIG. 5 in a second depressed position.

FIG. 7 is a diagram of the example dispensing apparatus 500 of FIG. 5 in a second depressed position. As depicted in FIG. 7, depressing the plunger 530 to a second depressed position may enable a second reagent to evacuate second chamber 510-2 of housing 520 and/or to elute (e.g. applied to, mix with, etc.) a sample. A reagent may evacuate the second chamber 510-2 when a seal formed by contact between the internal cavity of the housing and the first seal 450-1 is broken (e.g. compromised, lost, becomes unsealed, etc.). Depressing the plunger 530 from a first depressed position to the second depressed position may require a user to disengage safety mechanisms and/or ensure safety mechanisms are disengaged, which may require the user to operate the plunger 530 to permit tab 430-1 and tab 430-2 to pass through aperture 200, which may include a keyway (not shown), and/or may require a user to depress flexible tab 435-1 to permit flexible tab 435-1 to pass through aperture 200. Depressing the plunger 530 from the first depressed position to the second depressed position may also require the user to apply sufficient force to plunger 530 to enable first flange 540-1 and first seal 450-1 to move past protrusions 304 (not shown). The user may determine that the dispensing apparatus 110 is in the second depressed position when the cap 410 contacts housing 520, which may prevent a user from further depressing plunger 530 into housing 520.

FIG. 8 is a diagram of an example dispensing apparatus with one chamber according to an implementation described herein. As depicted in FIG. 8, dispensing apparatus 800 may include a plunger 820 and a housing 810. Dispensing apparatus 800 may be similar to dispensing apparatus 500 depicted in FIG. 5 except that dispensing apparatus 800 may have one chamber rather than two chambers because the plunger of dispensing apparatus 800 may have only one flange and/or seal. Plunger 820 may include a cap 821, a first member 822, tabs 823, a flange 824, a seal 825, a second member 826 and a tip 827. Housing 810 may include a penetration 811, a chamber 812, a protrusion 813, a gap 814 and a frangible seal 815.

Figure 9:
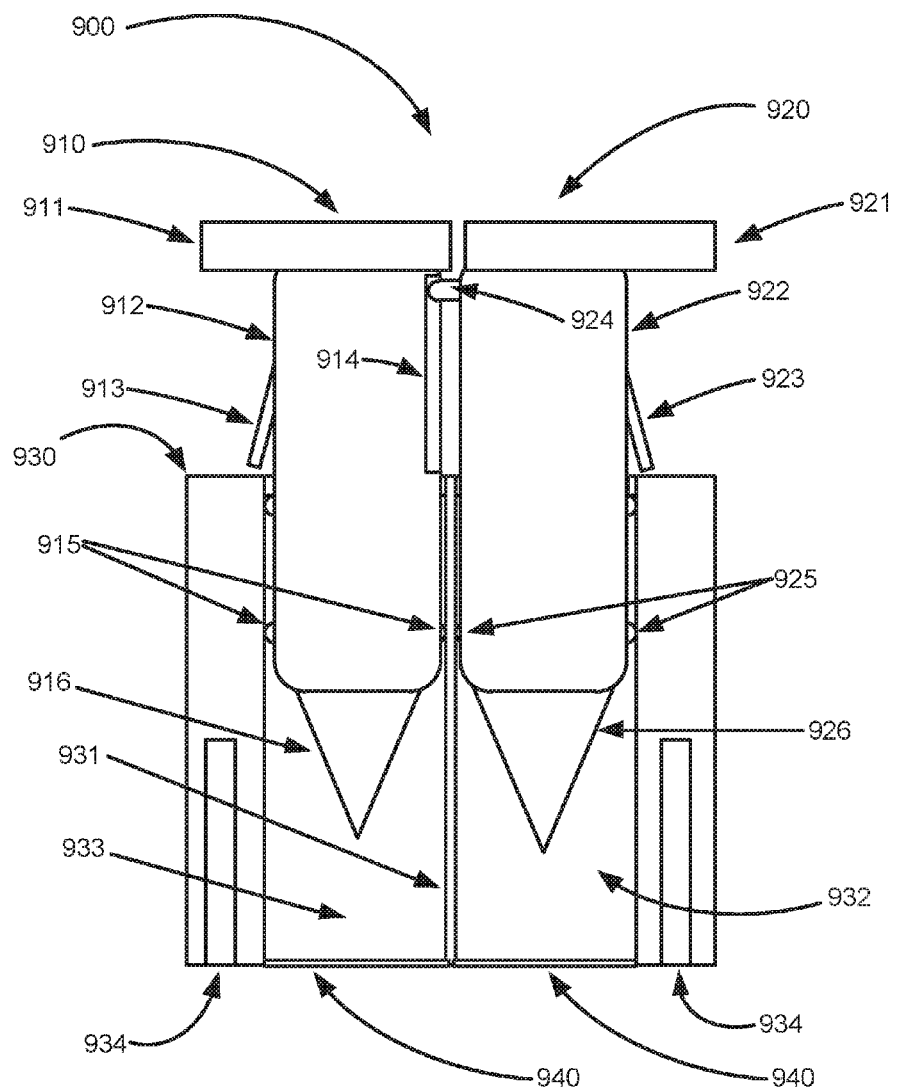
FIG. 9 is a diagram of yet another example dispensing apparatus with two chambers according to an implementation described herein.

FIG. 9 is a diagram of yet another example dispensing apparatus with two chambers according to an implementation described herein. Dispensing apparatus 900 may include a first plunger 920, a second plunger 910 and a side-by-side housing 930. First plunger 920 may be depressed into a first chamber 932 of side-by-side housing 930 by a user to evacuate a reagent stored within the first chamber 932 through a frangible seal 940. Second plunger 910 may be depressed into a second chamber 933 of side-by-side housing 930 by a user to evacuate a second reagent stored within the second chamber 933.

First plunger 920 may include a first cap 921, a first body 922, a first tab 923, a pin 924, first sealing surfaces 925, and a first tip 926. First plunger 920 may be formed by a material of sufficient rigidity and strength to support the weight of the side-by-side housing 930, reagents, other components, and/or any static and/or dynamic loads (e.g., forces, torques, tensions, compressions, etc.) imparted on the first plunger 920 while using the dispensing apparatus 900, such as a depression force. First plunger 920 may, for example, be made of polymer, metal, composite, wood, or some combination thereof. First plunger 920 may also, or alternatively, include transparent or translucent material. The strength and/or rigidity of the material may enable the first plunger 920 to maintain a basic shape when being used and/or to enable various components to be attached to the first plunger 920 and to be used. The first plunger 920 may assume any shape or volume. Additionally, or alternatively, the contours of the first plunger 920 may be straight and/or curved in a concave and/or convex manner.

A user may apply a force to first cap 921 to depress first plunger 920 into a depressed position. In a depressed position, first plunger 920 is depressed into first chamber 932 until the first cap 921 contacts side-by-side housing 930 and/or until first plunger 920 cannot extend further into first chamber 932. Also in depressed position, first tip 926 may penetrate and/or break seal 940, which may enable a first reagent to evacuate first chamber 932. First plunger may have first tab 923 which may act as a safety mechanism to prevent a reagent from being evacuated prematurely and/or unintentionally, such as during shipping, handling, etc. (e.g., by preventing the first tip 926 from penetrating the seal 940) by preventing first plunger 920 from passing through an opening in side-by-side housing 930 unless first tab 923 is depressed, properly aligned, and/or otherwise operated to permit first tab 923 to pass through an opening in side-by-side housing 930. For example, side-by-side housing 930 may have a keyway, such as keyway 202 of aperture 200 in FIG. 2, which may be permit first tab 923 to pass through whenever it is properly aligned with keyway. A user may align first tab 923 with the keyway to depress first plunger 920. Additionally, or alternatively, user may depress first tab 923 which may allow it to enter first chamber 932 when first plunger 920 is depressed. A user may depress, shift or apply force to first tab 923 in a manner that causes first tab 923 to move to a position where first tab 923 may align with and/or enter a cavity or depression within side-by-side housing 930. When first tab 923 is in this position, the first plunger 920 may be enabled to further move into and/or enter first chamber 932. Thus, first tab 923 may prevent first tip 926 from inadvertently contacting and/or penetrating seal 940, may prevent dispensing apparatus 900 from moving from an undepressed position to a depressed position, and/or may prevent dispensing apparatus 900 from releasing a reagent.

Pin 924 may extend from first plunger 920 into a slot 914 in second plunger 910. Pin 924 may prevent second plunger 910 from being depressed until first plunger 920 is depressed. When first plunger 920 is being depressed by a user, pin 924 may move from a first position at one end of slot 914 proximate second cap 911 to a second position at the opposite end of slot 914. When first plunger 920 is undepressed, pin 924 may reside in first position. When pin 924 is in first position, pin 924 may prevent a user from depressing second plunger 910 by contacting an upper surface of slot 914. When first plunger 920 is depressed, second plunger 910 may be depressed because pin 924 will no longer contact the upper surface of slot 914. In this way, pin 924 and slot 914 may prevent a second reagent in second chamber 933 from being evacuated by a user until after a first reagent in first chamber 932 is released.

First sealing surfaces 925 may be designed to fit within first chamber 932 and may contact an interior surface of first chamber 932 to form a sterile, an airtight, and/or liquid tight seal, within first chamber 932 when first plunger 920 is placed within side-by-side housing 930. First sealing surfaces 925 may allow first chamber 932 to store and/or contain one or more reagents and prevent the reagents from leaking out of and/or prematurely exiting the chamber. First sealing surfaces 925 may be temporarily and/or permanently attached to first body 922. First sealing surfaces 925 may be formed from any form or material (e.g., rubber seals, extrusions, lathe-cuts, gaskets, packing, Teflon® seals, mechanical seals, graphite, cloth, metal seals, metal rings, oil seals, elastomer seals, piston seals, quad rings, etc.) that may form a seal within a chamber. First sealing surfaces 925 may be formed as part of the first body 922 or may be a separate component that is temporarily or permanently attached to the first body 922.

First tip 926 may include and/or form a mechanism that that is sufficiently sharp to easily penetrate and/or break a seal 940. For example, second tip 926 may include a point, conical shape, knife, etc.

Second plunger 910 may include a second cap 911, a second body 912, a second tab 913, a slot 914, second sealing surfaces 915, and a second tip 916. Second plunger 910 may be formed by a material of sufficient rigidity and strength to support the weight of the side-by-side housing 930, reagents, other components, and/or any static and/or dynamic loads (e.g., forces, torques, tensions, compressions, etc.) imparted on the second plunger 910 while using the dispensing apparatus 900, such as a depression force. Second plunger 910 may, for example, be made of polymer, metal, composite, wood, or some combination thereof. Second plunger 910 may also, or alternatively, include transparent or translucent material. The strength and/or rigidity of the material may enable the second plunger 910 to maintain a basic shape when being used and/or to enable various components to be attached to the second plunger 910 and to be used. The second plunger 910 may assume any shape or volume. Additionally, or alternatively, the contours of the second plunger 910 may be straight and/or curved in a concave and/or convex manner.

A user may apply a force to second cap 911 to depress second plunger 910 into a depressed position. In a depressed position, second plunger 910 is depressed into second chamber 933 until the second cap 911 contacts side-by-side housing 930 and/or until second plunger 910 otherwise cannot extend further into second chamber 933. Also in depressed position, second tip 916 may penetrate and/or break seal 940, which may cause a second reagent to evacuate second chamber 933. Second plunger may have a second tab 913 which may act as a safety mechanism to prevent a reagent from being evacuated prematurely and/or unintentionally, such as during shipping, handling, etc. (e.g., by preventing the second tip 916 from penetrating the seal 940) by preventing second plunger 910 from passing through an opening in side-by-side housing 930 unless second tab 913 is depressed, properly aligned, and/or otherwise operated to permit second tab 913 to pass through an opening in side-by-side housing 930. For example, side-by-side housing 930 may have a keyway, such as keyway 202 of aperture 200 in FIG. 2, which may be permit second tab 913 to pass through whenever it is properly aligned with keyway. A user may align second tab 913 with the keyway to depress second plunger 910. Additionally, or alternatively, a user may depress second tab 913 which may allow it to enter second chamber 933 when second plunger 910 is depressed. A user may depress, shift or apply force to second tab 913 in a manner that causes second tab 913 to move to a position where second tab 913 may align with and/or enter a cavity or depression within side-by-side housing 930. When second tab 913 is in this position, the second plunger 910 may be depressed to further move into second chamber 933. Thus, second tab 913 may prevent second tip 916 from inadvertently contacting and/or penetrating seal 940 and/or may prevent dispensing apparatus 900 from releasing a reagent.

Slot 914 may be an indentation in second plunger 910 in which pin 924 may reside. Slot may have a first end and a second end opposite the first end. When first plunger 920 and second plunger are undepressed, as depicted in FIG. 9, pin 924 may reside at or near first end of slot 914. When first plunger 920 is depressed by a user, pin 924 may move from a first position at the first end of slot 914 to a second position at the second end of slot 914. When pin 924 is in first position, pin 924 may prevent a user from depressing second plunger 910 by contacting an upper surface of slot 914. When first plunger 920 is depressed, second plunger 910 may be depressed because pin 924 will no longer contact the upper surface of slot 914. In this way, pin 924 and slot 914 may ensure reagents are dispensed in a predetermined order by preventing a second reagent in second chamber 933 from being evacuated by a user until after a first reagent in first chamber 932 is evacuated.

Second sealing surfaces 915 may be designed to fit within second chamber 933 and may contact an interior surface of second chamber 933 to form a sterile, an airtight, and/or liquid tight seal, within second chamber 933 when second plunger 910 is placed within side-by-side housing 930. Second sealing surfaces 915 may allow second chamber 933 to store and/or contain one or more reagents and prevent the reagents from leaking out of and/or prematurely exiting the chamber. Second sealing surfaces 915 may be temporarily and/or permanently attached to second body 910. Second sealing surfaces 915 may be formed from any form or material (e.g., rubber seals, extrusions, lathe-cuts, gaskets, packing, Teflon® seals, mechanical seals, graphite, cloth, metal seals, metal rings, oil seals, elastomer seals, piston seals, quad rings, etc.) that may form a seal within a chamber. Second sealing surfaces 915 may be formed as part of the second body 912 or may be a separate component that is temporarily or permanently attached to second body 912.

Second tip 916 may include and/or form a mechanism that that is sufficiently sharp to easily penetrate and/or break a seal 940. For example, second tip 920 may include a point, conical shape, knife, etc.

Side-by-side housing 930 may include separating member 931, a first chamber 932, a second chamber 933, gap 934 and seal 940. A first reagent may reside within first chamber 931, and a second reagent may reside within second chamber 932. First chamber 932 may include an interior cavity with a first end and a second end that is opposite the first end. The first end may be covered with seal 940 (e.g., such as aluminum foil, mylar, polymer film, or some other material that can form a sterile, an airtight, and/or liquid tight seal) that does not react with a reagent. The second end may be open to allow a first plunger 920 to be inserted into first chamber 932 (e.g., during manufacture, assembly, thereafter, etc.). Similarly, second chamber 933 may include an interior cavity with a first end and a second end that is opposite the first end. The first end may be covered with seal 940 (e.g., such as aluminum foil, mylar, polymer film, or some other material that can form a sterile, an airtight, and/or liquid tight seal) that does not react with a reagent. Seal 940 covering the first end of the second chamber 933 may be the same piece of material as the seal 940 covering first end. Alternatively, seal 940 covering the first end of the second chamber 933 may be a separate piece of material from seal 940 covering first end of first chamber 932. The second end of the second chamber 933 may be open to allow a second plunger 910 to be inserted into second chamber 933 (e.g., during manufacture, assembly, thereafter, etc.).

In one embodiment, the side-by-side housing 930 may be a cylindrical shape, and the first chamber 932 and second chamber 933 may be half-cylindrical shapes and may fit inside the side-by-side housing 930. Additionally, or alternatively, side-by-side housing 930 may assume any shape or volume such as, for example, a cylinder, cube, orthotope, rectangular cuboid, rectangular parallelepiped, three dimension polygon, etc. Additionally, or alternatively, the contours of the side-by-side housing 930 may be straight and/or curved in a concave and/or convex manner. Similarly, first chamber 932 and second chamber 933 may assume any shape or volume such as, for example, a cylinder, cube, orthotope, rectangular cuboid, rectangular parallelepiped, three dimension polygon, etc. Additionally, or alternatively, the contours of the first chamber 932 and/or second chamber 933 may be straight and/or curved in a concave and/or convex manner. Additionally, or alternatively, the cross-sectional area of the first chamber 932 and/or the second chamber 933 may increases from one end of the chamber proximate the frangible to an opposite end of the chamber, which may increase the force needed to depress first plunger 920 and/or second plunger 910 into first chamber 932 and second chamber 933, respectively as the first plunger 920 and second plunger 910 become further depressed.

Separating member 931 may separate and/or form a barrier between first chamber 932 from second chamber 933. Separating member 931 may be connected to seal 940 to form a barrier between first chamber 932 and second chamber 933. Additionally, or alternatively, separating member 931 may be connected to seal 940 so that when first tip 832 pieces the portion of seal 940 covering first chamber 932, the portion of seal 940 covering second chamber 933 is not pierced.

Gap 934 may receive a container, such as container 140, and/or connect the container to the dispensing device 900 (e.g. threaded attachment, compression fit, adhesives, etc.). The container, such as container 140 of FIGS. 1A and 1B, may, for example, contain a sample and/or allow insert of a sample into the container 140 such that the first reagent may be released from the first chamber 932 and/or the second reagent may be released from the second chamber into the container and/or applied to the sample.

In an alternative embodiment, the first reagent in the first chamber 932 and the second reagent in the second chamber 933 may be stored in a pierceable insert (e.g., bulb, capsule, tablet, portable reservoir, etc.) that may be pierced when the first plunger and second plunger, respectively, are depressed, which pierces the insert to release reagent contained therein. In this embodiment, a pierceable insert may be inserted into the first chamber and another pierceable insert inserted into the second chamber such that the user of the dispensing apparatus (e.g., via the plunger) may control when the reagent is released and/or applied to a sample in a manner that is appropriate for the assay. For example, depression of a plunger may cause the pierceable insert to be pierced, the first seal (e.g., frangible seal) to be broken, and/or to allow the reagent to evacuate from the chamber. Additionally, or alternatively, in one non-liming implementation, the pierceable inserts may include a piercing component (e.g., sharp element, point, knife, etc.) and/or the pierceable insert-piercing component assembly may be separate from the plunger and/or the member. In this embodiment, the first plunger and second plunger may not have a piercing component. Depression of the plunger may cause the plunger to contact the pierceable insert which may cause the piercing component to pierce the pierceable insert and/or the first seal (e.g., frangible seal) to allow a reagent to evacuate the chamber.

The foregoing description provides illustration and description, but is not intended to be exhaustive or to limit the implementations to the precise form disclosed. Modifications and variations are possible in light of the above disclosure or may be acquired from practice of the embodiments.

It will be apparent that technologies and/or techniques, as described above, may be implemented in many different forms of hardware in the implementations illustrated in the figures. The actual or specialized hardware used to implement these technologies and/or techniques is not limiting of the embodiments—it being understood that hardware can be designed to implement the technologies and/or techniques based on the description herein.

It should be emphasized that the terms "comprises"/ "comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" and "an" are intended to include one or more items and may be used interchangeably with "one" or "more." Where only one item is intended, the term "one" or similar language is used. Further, the phrase "based on" is intended to mean "based, at least in part on" unless explicitly stated otherwise.

The number of components illustrated in FIGS. 1-9 is provided for explanatory purposes only and the disclosure herein not intended to be limited to the components illustrated in FIGS. 1-9. There may be additional components, fewer components, different components, or differently arranged components than illustrated in FIGS. 1-9. Also, in some implementations, one or more of the components of the dispensing apparatus may perform one or more functions described as being performed by another one or more of the components of the dispensing apparatus.

Additionally, alternatively, the embodiments of the dispensing apparatus shown in FIGS. 1-9 may be combined. For example, the dispensing apparatus may include two or more chambers side-by-side, where each chamber includes sub-chambers that are aligned longitudinally.

What is claimed is:

1. A reagent dispensing apparatus for performing an assay on a sample, taken from a patient, using two or more reagents, the reagent dispensing apparatus comprising:
   a housing that includes an internal cavity having a first end with an opening and a second end that is opposite the first end, the second end including an aperture;
   a plunger that includes:
      a first member that fits through the aperture and includes a third end and a fourth end that is opposite the third end,
         the third end being outside the housing, and
         the fourth being located within the internal cavity and is associated with a first seal,
      one or more safety mechanisms associated with the first member that, when engaged, prevent movement of the first member through the aperture, and, when disengaged, permit movement of the first member through the aperture, and
      a second member that is within the internal cavity and includes a fifth end and a sixth end that is opposite the fifth end,
         the fifth end being associated with the first seal, and
         the sixth end being associated with a second seal, the first seal and the second seal forming a first chamber, within a first portion of the internal cavity, that stores a first reagent; and
   a frangible seal that covers the opening of the internal cavity, the frangible seal and the second seal forming a second chamber, within a second portion of the internal cavity, that stores a second reagent,
      the frangible seal being breached when the third end is depressed and the one or more safety mechanisms are disengaged to enable the plunger to move from an undepressed position to a first depressed position and causing the second reagent to exit the chamber through the opening and elute the sample, and
      the first reagent exiting the first chamber, through the opening, to elute the sample when the one or more safety mechanisms are disengaged and the third end is further depressed to enable the plunger to move from the first depressed position to a second depressed position.

2. The reagent dispensing apparatus of claim 1, further comprising a container in which the sample is stored and into which the first reagent and the second reagent may be evacuated in a predetermined sequence.

3. The reagent dispensing apparatus of claim 1, where the one or more safety mechanisms comprise:

a pair of tabs; and
a keyway, associated with the aperture, through which each tab of the pair of tabs may move when the two sets of two safety tabs are disengaged and when the plunger is depressed.

4. The reagent dispensing apparatus of claim 3, where a longitudinal distance between each tab of the pair of tabs is greater than or equal to a thickness of an upper surface of the housing.

5. The reagent dispensing apparatus of claim 1, where the one or more safety mechanisms comprise a flexible tab that may be depressed to disengage the flexible tab.

6. The reagent dispensing apparatus of claim 1, where at least one of the first seal or second seal include an O-ring.

7. The reagent dispensing apparatus of claim 1, where at least one of the first seal or second seal include a flange.

8. The reagent dispensing apparatus of claim 1, where the housing includes a protrusion within the chamber.

9. The reagent dispensing apparatus of claim 1, where the housing includes a gap to which the container may be connected.

10. The reagent dispensing apparatus of claim 1, where the third end is connected to a cap.

11. A reagent dispensing apparatus comprising:
a housing that includes an internal cavity having a first end with an opening and a second end that is opposite the first end, the second end including an aperture;
a plunger that moves through the cavity, the plunger including:
a first member that includes a third end that is outside of the housing, a fourth end opposite the third end, and two or more safety mechanisms that prevent movement of the first member when the two or more safety mechanisms are engaged,
the fourth end being associated with a first seal inside the internal cavity, and
a second member, inside the cavity, that includes a fifth end that is associated with the first seal and a sixth end, opposite the fifth end, that is associated with a second seal,
the first seal and the second seal forming a first chamber, within a first portion of the internal cavity, that stores a first reagent, and
the second seal being associated with a tip; and
a frangible seal that covers the opening of the internal cavity, the frangible seal and the second seal forming a second chamber, within a second portion of the internal cavity, that stores a second reagent,
the frangible seal being pierced when a first safety mechanism, of the two or more safety mechanisms, is disengaged and the third end is depressed to enable the plunger to move causing the tip to pierce the frangible seal and the second reagent to exit the chamber through the opening, and
the second seal being broken when a second safety mechanism, of the two or more safety mechanisms, is disengaged and the third end is further depressed to enable the first reagent to exit the first chamber through the opening.

12. The reagent dispensing apparatus of claim 11, where the housing includes a protrusion which increases the force required to depress the plunger from either the undepressed position to the first depressed position, from the first depressed position to the second depressed position, or both.

13. The reagent dispensing device of claim 11, further comprising:

a first flange connected to the fourth end and fifth end, the first seal associated with a perimeter of the first flange; and
a second flange connected to the sixth end and the tip, the second seal associated with a second perimeter of the second flange.

14. The reagent dispensing device of claim 11, where the first safety mechanism includes a tab and a keyway and the second safety mechanism includes a flexible tab.

15. The reagent dispensing apparatus of claim 11, where the two or more safety mechanisms comprise:
two tabs; and
a keyway, associated with the aperture, through which the two tabs move when the two tabs are in a disengaged position and when the plunger is depressed.

16. The reagent dispensing apparatus of claim 15, where a longitudinal distance between the two tabs is greater than or equal to a thickness of an upper surface of the housing.

17. The reagent dispensing apparatus of claim 11, where at least one of the first seal or second seal includes an O-ring.

18. A reagent dispensing apparatus comprising:
a housing that includes an internal cavity having a first end with an opening and second end that is opposite the first end, the second end including an aperture;
a plunger that is movable within the cavity, the plunger including:
a first member that includes a third end, a fourth end opposite the third end, and two or more safety mechanisms,
the fourth end being associated with a first seal,
the two or more safety mechanisms including at least one of,
a first safety mechanism associated with a first tab that is flexible, the first safety mechanism being disengaged when the first tab is depressed, and
a second safety mechanism that corresponds to a keyway associated with the aperture and second tab that is not flexible, the second safety mechanism is disengaged when the second tab is aligned with the keyway,
a second member that includes a fifth end that is associated with the first seal and a sixth end, opposite the fifth end, that is associated with a second seal,
the first seal and the second seal forming a first chamber, within a first portion of the internal cavity, that stores a first reagent,
the second seal being associated with a tip; and
a frangible seal that covers the opening of the internal cavity, the frangible seal and the second seal forming a second chamber, within a second portion of the internal cavity, that stores a second reagent,
the frangible seal being pierced when one of the two or more safety mechanisms is disengaged and the third end is depressed to enable the plunger to move within the cavity causing the tip to pierce the frangible seal and evacuate the second reagent from the second chamber, and
the second seal being broken when a different one of the two or more safety mechanisms is disengaged and the third end is further depressed to enable the first reagent to exit the first chamber through the opening.

19. The reagent dispensing device of claim 18 further comprising:
a first flange connected to the fourth end and fifth end, the first seal associated with a perimeter of the first flange; and a second flange connected to the sixth end and the tip, the second seal associated with a second perimeter of the second flange.

20. The reagent dispensing device of claim 18, where at least one of the first seal or second seal includes an O-ring.

21. A method for administering two or more reagents to a sample in a predetermined order, the method comprising:
providing a dispensing apparatus comprising:
a housing that includes an internal cavity having a first end with an opening and a second end that is opposite the first end, the second end including an aperture;
a plunger that includes:
a first member that includes a third end, a fourth end opposite the third end, and one or more safety mechanisms,
the third end, when depressed, causing the first member to move through the aperture when the one or more safety mechanisms are disengaged, and the fourth end being associated with a first seal,
the one or more safety mechanisms, when engaged, prevent movement of the first member through the aperture and, when disengaged, permit movement of the first member through the aperture,
a second member that includes a fifth end that is associated with the first seal and a sixth end, opposite the fifth end, that is associated with a second seal,
the first seal and the second seal forming a first chamber, within a first portion of the internal cavity, that stores a first reagent, and
a frangible seal that covers the opening of the internal cavity, the frangible seal and the second seal forming a second chamber, within a second portion of the internal cavity, that stores a second reagent;
providing a container containing a sample, the container capable of receiving the first reagent and the second reagent from the dispensing apparatus;
operating the dispensing apparatus to move the plunger from an undepressed position to a first depressed position to apply the second reagent to the sample, where moving the plunger from the undepressed position to the first depressed position includes ensuring the one or more safety mechanisms are disengaged, depressing the third end, breaching the frangible seal, and evacuating the second reagent from the housing through the opening to apply the second reagent to the sample; and
operating the dispensing apparatus to move the plunger from the first depressed position to a second depressed position to apply the first reagent to the sample, where moving the plunger from the first depressed position to the second depressed position includes ensuring the one or more safety mechanisms are disengaged, depressing the third end, and evacuating the first reagent from the housing through the opening to apply the first reagent to the sample.

22. The method for administering two or more reagents to a sample in a predetermined order of claim 21, the method further comprising:
aligning a first safety mechanism, of the one or more safety mechanisms, with a keyway associated with the aperture, to ensure that the first safety mechanism is disengaged prior to applying the second reagent to the sample; and
rotating the plunger, the housing, or both to align a second safety mechanism, of the one or more safety mechanisms, with the keyway to ensure that the second safety mechanisms is disengaged prior to applying the first reagent to the sample.

\* \* \* \* \*